(12) United States Patent
Lantzsch et al.

(10) Patent No.: US 7,501,527 B2
(45) Date of Patent: Mar. 10, 2009

(54) METHOD FOR THE PRODUCTION OF FLUOROMETHYL-SUBSTITUTED HETEROCYCLES

(75) Inventors: Reinhard Lantzsch, Wuppertal (DE); Sergiy Pazenok, Solingen (DE); Frank Memmel, Guntersblum (DE)

(73) Assignee: Bayer CropScience GmbH, Frankfurt (DE)

( * ) Notice: Subject to any disclaimer, the term of this patent is extended or adjusted under 35 U.S.C. 154(b) by 10 days.

(21) Appl. No.: 10/576,742

(22) PCT Filed: Oct. 19, 2004

(86) PCT No.: PCT/EP2004/011809

§ 371 (c)(1), (2), (4) Date: Aug. 28, 2006

(87) PCT Pub. No.: WO2005/044804

PCT Pub. Date: May 19, 2005

(65) Prior Publication Data

US 2006/0276656 A1    Dec. 7, 2006

(30) Foreign Application Priority Data

Oct. 31, 2003    (DE)    ................ 103 51 088

(51) Int. Cl.
*C07D 231/12*    (2006.01)
(52) U.S. Cl. .................................. 548/374.1
(58) Field of Classification Search ........... 548/374.1
See application file for complete search history.

(56) References Cited

U.S. PATENT DOCUMENTS

| | | | | |
|---|---|---|---|---|
| 5,093,347 A | 3/1992 | Graneto et al. | ............... | 514/406 |
| 5,223,526 A | 6/1993 | McLoughlin et al. | ....... | 514/406 |
| 5,675,016 A | 10/1997 | Gallenkamp et al. | ..... | 548/374.1 |
| 6,319,940 B1 | 11/2001 | Elbe et al. | .................... | 514/406 |
| 6,417,361 B1 * | 7/2002 | Hayashi et al. | ............. | 544/334 |

FOREIGN PATENT DOCUMENTS

| | | |
|---|---|---|
| DE | 39 34 924 A1 | 4/1991 |
| WO | 03/070705 A1 | 8/2003 |

OTHER PUBLICATIONS

Ishii et al., CA 111:194759, 1989.*

\* cited by examiner

*Primary Examiner*—Laura L. Stockton
(74) *Attorney, Agent, or Firm*—Richard E. L. Henderson

(57) ABSTRACT

The present invention relates to a process for preparing fluoromethyl-substituted heterocycles of the formula (I)

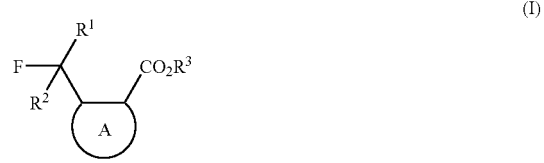

in which $R^1$, $R^2$, $R^3$ and A are each as defined in the disclosure, by fluorinating the corresponding chloromethyl-substituted precursors.

7 Claims, No Drawings

METHOD FOR THE PRODUCTION OF FLUOROMETHYL-SUBSTITUTED HETEROCYCLES

The present patent application has been filed under 35 U.S.C. 371 as a national stage application of PCT/EP2004/011809, filed Oct. 19, 2004, which was published in German as International Patent Publication WO 2005/044804 on May 19, 2005, and is entitled to the right of priority of German Patent Application 10351 088.5, filed Oct. 31, 2003.

The present invention relates to a novel process for preparing fluoromethyl-substituted heterocycles by reacting the corresponding chloromethyl-substituted compound with a fluorinating agent.

It is already known that 3-(difluoromethyl)- and 3-(fluorodichloromethyl)-1-methyl-1H-pyrazole-4-carboxylic esters can be obtained by reacting the correspondingly halogenated 2-(ethoxymethylene)methyl acetoacetate with methylhydrazine (cf. WO 92/12970 and WO 93/11117).

It is also known that 5-chloropyrazole-4-carboxaldehyde derivatives can be reacted with potassium fluoride in dimethylformamide to give the corresponding 5-fluoro compound (cf. WO 93/11117).

The conversion of heterocycles which are substituted by mono-, di- or trichloromethyl to fluorinated analogues is known hitherto only for pyridine derivatives. Since chlorinated precursors are frequently more readily available than the corresponding fluorine compounds for the preparation of heterocycles, there is a need for a process which allows chlorinated heterocycles to be directly fluorinated.

The present invention thus provides a process for preparing fluoromethyl-substituted heterocycles of the formula (I)

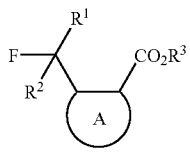

(I)

in which
$R^1$ is hydrogen, fluorine or chlorine,
$R^2$ is hydrogen, fluorine or chlorine,
$R^3$ is $C_1$-$C_6$-alkyl,
A is 5-membered heterocycle selected from the group of pyrazole which is substituted by $R^4$ in the 1-position, thiazole which is substituted by $R^4$ in the 2-position and oxazole which is substituted by $R^4$ in the 2-position,
$R^4$ is $C_1$-$C_4$-alkyl, $C_3$-$C_6$-cycloalkyl, $C_1$-$C_4$-alkylthio-$C_1$-$C_4$-alkyl, $C_1$-$C_4$-alkoxy-$C_1$-$C_4$-alkyl or phenyl, characterized in that
a) chloromethyl-substituted heterocycles of the formula (II)

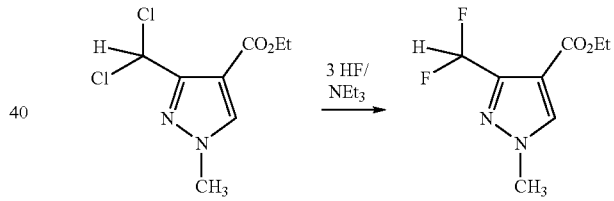

(II)

in which $R^1$, $R^2$, $R^3$ and A are each as defined above are converted in the presence of a fluorinating agent and optionally in the presence of a diluent.

Surprisingly, the fluoromethyl-substituted heterocycles of the formula (I) can be prepared with good yields in high purity and selectivity under the inventive conditions. Although the preparation of trifluoromethyl-, difluoromethyl- or monofluoromethyl-substituted aromatic compounds from the correspondingly chlorinated compounds by halogen exchange is known for phenyl- and some 3-trihaloalkylpyridine derivatives, it is necessary in these processes to employ severe conditions such as the use of HF, high temperatures and pressure. Under these reaction conditions, those skilled in the art, in the case of pyrazole, thiazole and other heterocyclic compounds which are substituted by trichloromethyl or by the more sensitive and less stable dichloromethyl, would expect the decomposition of the heterocycle (for example by polymerization, hydrolysis or the formation of acids and aldehydes). This decomposition process is even accelerated when, for example, a dichloromethyl group is conjugated directly with an electron pair of a nitrogen atom, as is the case for 3-haloalkyl-substituted pyrazoles. In addition, the fluorination of compounds having a substituent in the ortho-position, especially when it is the large and electron-withdrawing carboxylic ester group, is distinctly more difficult to carry out for steric and electronic reasons. This is because the carboxylic ester group is normally hydrolysed under strongly acidic conditions (for example when HF or its derivatives are used) and forms a ring with the adjacent trichloromethyl or dichloromethyl group: It is all the more surprising that the fluoromethyl-substituted heterocycles of the formula (I) can be obtained in good yields by the process according to the invention.

When, for example, ethyl 3-(dichloromethyl)-1-methyl-1H-pyrazole-4-carboxylate is used as a starting material and triethylamine (tris)hydrofluoride as the fluorinating agent, the process according to the invention (a) may be illustrated by the following scheme.

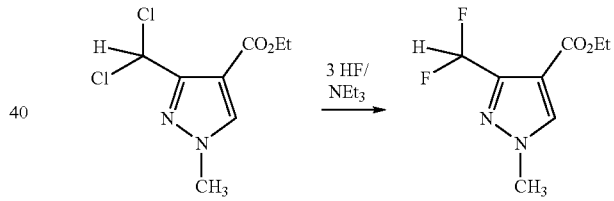

The chloromethyl-substituted heterocycles used as starting materials when carrying out the process according to the invention are generally defined by the formula (II). The substituents have the following preferred definitions:

$R^1$ is preferably hydrogen, fluorine or chlorine.
$R^2$ is preferably hydrogen, fluorine or chlorine.
$R^3$ is preferably $C_1$-$C_4$-alkyl, more preferably methyl, ethyl, n-propyl, isopropyl, n-butyl, sec-butyl, isobutyl or tert-butyl, most preferably methyl or ethyl.
A is preferably a 5-membered heterocycle selected from the group of

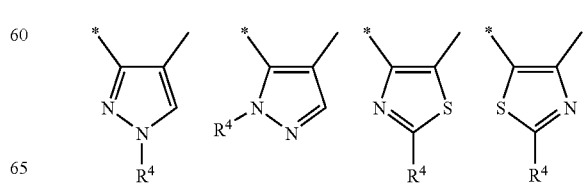

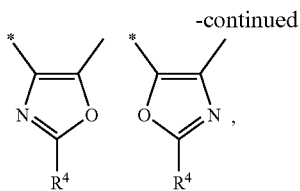

more preferably a 5-membered heterocycle selected from the group of

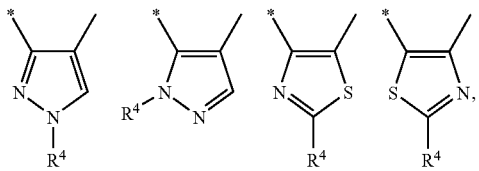

most preferably a 5-membered heterocycle selected from the group of

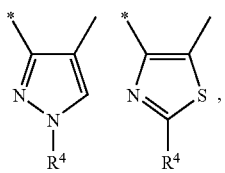

where in each case the bond marked by * is joined to the —CClR$^1$R$^2$ group and the other bond to the ester group, R$^4$ is preferably methyl, ethyl, n-propyl, isopropyl, cyclopropyl, cyclopentyl, cyclohexyl or phenyl, more preferably methyl, ethyl, isopropyl or phenyl, most preferably methyl.

The starting material used is preferably a chloromethyl-substituted heterocycle of the formula (II) in which R$^1$ is chlorine and R$^2$ is hydrogen.

Particularly preferred starting materials of the formula (II) are chloromethyl-substituted heterocycles of the formula (II-a)

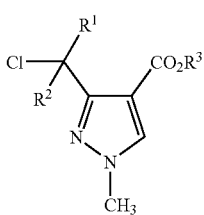

(II-a)

in which R$^1$, R$^2$ and R$^3$ are each as defined above.

Very particular preference is given to compounds of the formula (II-a) in which R$^1$ is chlorine, R$^2$ is hydrogen and R$^3$ is methyl or ethyl.

Particularly preferred starting materials of the formula (II) are likewise chloromethyl-substituted heterocycles of the formula (II-b)

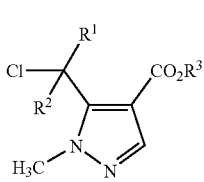

(II-b)

in which R$^1$, R$^2$ and R$^3$ are each as defined above.

Very particular preference is given to compounds of the formula (II-b) in which R$^1$ is chlorine, R$^2$ is hydrogen and R$^3$ is methyl or ethyl.

Particularly preferred starting materials of the formula (II) are likewise chloromethyl-substituted heterocycles of the formula (II-c)

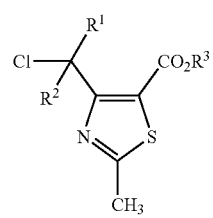

(II-c)

in which R$^1$, R$^2$ and R$^3$ are each as defined above.

Very particular preference is given to compounds of the formula (II-c) in which R$^1$ is chlorine, R$^2$ is hydrogen and R$^3$ is methyl or ethyl.

Particularly preferred starting materials of the formula (II) are likewise chloromethyl-substituted heterocycles of the formula (II-d)

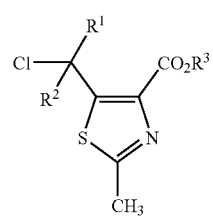

(II-d)

in which R$^1$, R$^2$ and R$^3$ are each as defined above.

Very particular preference is given to compounds of the formula (II-d) in which R$^1$ is chlorine, R$^2$ is hydrogen and R$^3$ is methyl or ethyl.

Some chloromethyl-substituted heterocycles of the formula (II) are known (cf. WO 92/12970, WO 93/11117 and The Chemistry of Heterocyclic Compounds: Thiazole and its derivatives, Jaques Metzger (ed.), Vol. 34, Part 1-3, John Wiley and Sons, New York, 1979).

3-Halomethyl-1H-pyrazole-4-carboxylic esters can be prepared by b) reacting acid halides of the formula (III)

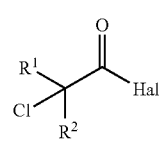

(III)

in which
R$^1$ and R$^2$ are each as defined above,
Hal is fluorine, chlorine or bromine, with dialkylaminoacrylic esters of the formula (IV)

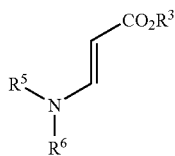

(IV)

in which
R³ is as defined above,
R⁵ and R⁶ are each independently $C_1$-$C_4$-alkyl in a water-inmiscible organic solvent (for example toluene) in the presence of a base (for example sodium hydroxide or pyridine),
and reacting the thus obtained 2-dihaloacyl-3-aminoacrylic esters of the formula (V)

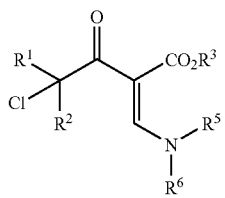

(V)

in which $R^1$, $R^2$, $R^3$, $R^5$ and $R^6$ are as each as defined above with hydrazine derivatives of the formula (VI)

(VI)

in which $R^4$ is as defined above in the presence of a diluent (for example toluene).

The process (a) according to the invention is carried out in the presence of a fluorinating agent. Useful for this purpose are all customary fluorinating agents for such reactions. Preference is given to using, for example, alkali metal fluorides such as sodium fluoride, potassium fluoride and caesium fluoride, cobalt(III) fluoride, halogen fluorides, antimony fluorides, molybdenum fluoride, hydrogen fluoride, hydrogen fluoride/pyridine mixtures, tertiary ammonium hydrofluorides or trialkylamine hydrofluorides of the general formula n HF/N(Alk)₃ (where n is 1, 2, or 3, preferably 2 or 3, and Alk is $C_1$-$C_4$-alkyl, preferably ethyl or n-butyl). Particular preference is given to using 3 HF/N(Et)₃ (Franz reagent), 3 HF/N(n-Bu)₃ and HF/pyridine (Olah's reagent). Very particular preference is given to using 3 HF/N(Et)₃ (Franz reagent) or 3 HF/N(n-Bu)₃.

The process according to the invention is optionally carried out in the presence of a diluent. Preference is given to using nitriles such as acetonitrile; halogenated hydrocarbons, for example chlorobenzene, dichlorobenzene, dichloromethane, chloroform, tetrachloromethane, dichloroethane, trifluorochloromethane, 1,1,2-trifluoro-1,2,2-trichloroethane, 1,1,1-trifluoro-2,2,2-trichloroethane or trichloroethane; aromatic hydrocarbons, for example petroleum ether, hexane, heptane, cyclohexane, methylcyclohexane, benzene, toluene, xylene or decalin; ethers such as diethyl ether, diisopropyl ether, methyl tert-butyl ether, methyl tert-amyl ether, dioxane, tetrahydrofuran, 1,2-dimethoxyethane, 1,2-diethoxyethane or anisole; diethylene glycol. Particular preference is given to using acetonitrile, toluene, chlorobenzene, trifluorochloromethane, 1,1,2-trifluoro-1,2,2-trichloroethane, 1,1,1-trifluoro-2,2,2-trichloroethane, dioxane or diethylene glycol.

When carrying out the process according to the invention, it is possible to work within a relatively wide temperature range. In general, working temperatures are 80° C. to 170° C. or in the range of 20° C. to 170° C., preferably 120° C. to 150° C. or 100° C. to 150° C.

The process according to the invention is generally carried out under atmospheric pressure, However, it is also possible to work under elevated or reduced pressure, generally between 0.1 bar and 50 bar, preferably between 1 bar and 10 bar.

The reaction time is not critical and may be selected depending on the batch size within a relatively wide range of 1 h to 20 h, preferably of 6 h to 12 h.

When carrying out the process according to the invention, for 1 mol of chloromethyl-substituted heterocycles of the formula (II), generally between 1 mol and 3 mol of bound HF, preferably between 1 mol and 1.5 mol, of fluorinating agent are used per chlorine atom.

The fluoromethyl-substituted heterocycles of the formula (I)which can be prepared by the process according to the invention are valuable precursors for the preparation of halomethyl-substituted pyrazolyl-, thiazolyl- and oxazolylcarboxamides which constitute active fungicidal ingredients (cf. WO 03/070705).

For example, fungicidally active carboxamides of the formula (VII)

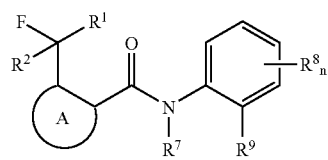

(VII)

in which
$R^1$, $R^2$ and A are each as defined above,
$R^7$ is hydrogen, $C_1$-$C_8$-alkyl, $C_1$-$C_6$-alkylsulphinyl, $C_1$-$C_6$-alkylsulphonyl, $C_1$-$C_4$-alkoxy-$C_1$-$C_4$-alkyl, $C_3$-$C_8$-cycloalkyl; $C_1$-$C_6$-haloalkyl, $C_1$-$C_4$-haloalkylthio, $C_1$-$C_4$-haloalkylsulphinyl, $C_1$-$C_4$-haloalkylsulphonyl, halo-$C_1$-$C_4$-alkoxy-$C_1$-$C_4$-alkyl, $C_3$-$C_8$-halocycloalkyl having in each case 1 to 9 fluorine, chlorine and/or bromine atoms; formyl, formyl-$C_1$-$C_3$-alkyl, ($C_1$-$C_3$-alkyl)carbonyl-$C_1$-$C_3$-alkyl, ($C_1$-$C_3$-alkoxy)carbonyl-$C_1$-$C_3$-alkyl; halo-($C_1$-$C_3$-alkyl)carbonyl-$C_1$-$C_3$-alkyl, halo-($C_1$-$C_3$-alkoxy)carbonyl-$C_1$-$C_3$-alkyl having in each case 1 to 13 fluorine, chlorine and/or bromine atoms; ($C_1$-$C_8$-alkyl)carbonyl, ($C_1$-$C_8$-alkoxy)carbonyl, ($C_1$-$C_4$-alkoxy-$C_1$-$C_4$-alkyl)carbonyl, ($C_3$-$C_8$-cycloalkyl)carbonyl; ($C_1$-$C_6$-haloalkyl)carbonyl, ($C_1$-$C_6$-haloalkoxy)carbonyl, (halo-$C_1$-$C_4$-alkoxy-$C_1$-$C_4$-alkyl)carbonyl, ($C_3$-$C_8$-halocycloalkyl)carbonyl having in each case 1 to 9 fluorine, chlorine and/or bromine atoms; or —C(=O)C(=O)$R^{10}$, —CONR$^{11}$R$^{12}$ or —CH₂NR$^{13}$R$^{14}$,
$R^8$ is hydrogen, fluorine, chlorine, methyl, isopropyl, methylthio or trifluoromethyl,
n is 1, 2, 3 or 4, preferably 1 or 2,
$R^9$ is optionally mono- to pentasubstituted phenyl having identical or different substituents which are selected from halogen, $C_1$-$C_4$-alkyl, $C_1$-$C_4$-alkoxy, $C_1$-$C_2$-haloalkyl or $C_1$-$C_2$-haloalkoxy having in each case 1 to 5 fluorine, chlorine and/or bromine atoms, hydroxyimino-$C_1$-$C_4$-alkyl, $C_1$-$C_4$-alkoxyimino-$C_1$-$C_4$-alkyl, $C_1$-$C_4$-haloalkoxyimino-$C_1$-$C_4$-alkyl, or, in the case of two adjacent substituents, from difluoromethylenedioxy or tetrafluoroethylenedioxy;
or is $C_3$-$C_{10}$-cycloalkyl or $C_3$-$C_{10}$-bicycloalkyl which is in each case optionally mono- to tetrasubstituted, identically or differently, by halogen and/or $C_1$-$C_4$-alkyl;
or unsubstituted $C_2$-$C_{20}$-alkyl, or $C_1$-$C_{20}$-alkyl which is mono- or polysubstituted, identically or differently, by fluorine, chlorine, bromine, iodine and/or $C_3$-$C_6$-cycloalkyl, in which case the cycloalkyl moiety may itself optionally be mono- to tetrasubstituted, identically or differently, by fluorine, chlorine, bromine, iodine, $C_1$-$C_4$-alkyl and/or $C_1$-$C_4$-haloalkyl;
or is $C_2$-$C_{20}$-alkenyl or $C_2$-$C_{20}$-alkynyl which is in each case optionally mono- or polysubstituted, identically or differently, by fluorine, chlorine, bromine, iodine and/or $C_3$-$C_6$-cycloalkyl in which case the cycloalkyl moiety may itself optionally be mono- to tetrasubstituted, identically or differently, by fluorine, chlorine, bromine, iodine, $C_1$-$C_4$-alkyl and/or $C_1$-$C_4$-haloalkyl;
$R^{10}$ is hydrogen, $C_1$-$C_8$-alkyl, $C_1$-$C_8$-alkoxy, $C_1$-$C_4$-alkoxy-$C_1$-$C_4$-alkyl, $C_3$-$C_8$-cycloalkyl; $C_1$-$C_6$-haloalkyl, $C_1$-$C_6$-haloalkoxy, halo-$C_1$-$C_4$-alkoxy-$C_1$-$C_4$-alkyl, $C_3$-$C_8$-halocycloalkyl having in each case 1 to 9 fluorine, chlorine and/or bromine atoms,
$R^{11}$ and $R^{12}$ are each independently hydrogen, $C_1$-$C_8$-alkyl, $C_1$-$C_4$-alkoxy-$C_1$-$C_4$-alkyl,$C_3$-$C_8$-cycloalkyl; $C_1$-$C_8$-haloalkyl, halo-$C_1$-$C_4$-alkoxy-$C_1$-$C_4$-alkyl, $C_3$-$C_8$-halocycloalkyl having in each case 1 to 9 fluorine, chlorine and/or bromine atoms,
$R^{11}$ and $R^{12}$ are also, together with the nitrogen atom to which they are bonded, a saturated heterocycle having 5 to 8 ring atoms which is optionally mono- or polysubstituted, identically or differently, by halogen or $C_1$-$C_4$-alkyl, and the heterocycle may contain 1 or 2 further, nonadjacent heteroatoms from the group of oxygen, sulphur and $NR^{15}$,
$R^{13}$ and $R^{14}$ are each independently nitrogen atom, $C_1$-$C_8$-alkyl, $C_3$-$C_8$-cycloalkyl; $C_1$-$C_8$-haloalkyl, $C_3$-$C_8$-halocycloalkyl having in each case 1 to 9 fluorine, chlorine and/or bromine atoms,
$R^{13}$ and $R^{14}$ are also, together with the nitrogen atom to which they are bonded, a saturated heterocycle having 5 to 8 ring atoms which is optionally mono- or polysubstituted, identically or differently, by halogen or $C_1$-$C_4$-alkyl, and the heterocycle may contain 1 or 2 further, nonadjacent heteroatoms from the group of oxygen, sulphur and $NR^{15}$,
$R^{15}$ is hydrogen or $C_1$-$C_6$-alkyl are obtained by hydrolyzing fluoromethyl-substituted heterocycles of the formula (I)

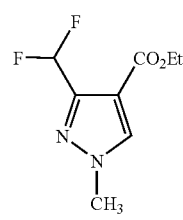

(I)

in which $R^1$, $R^2$, $R^3$ and A are each as defined above
in the presence of a base and optionally in the presence of a diluent, and subsequently either converting the free acid to the corresponding acid chloride in the presence of a chlorinating agent and optionally in the presence of a diluent or reacting the free acid directly with aniline derivatives of the formula (VIII)

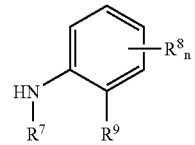

(VIII)

in which $R^7$, $R^8$, n and $R^9$ are each as defined above
optionally in the presence of a catalyst, optionally in the presence of a condensing agent, optionally in the presence of an acid binding agent and optionally in the presence of a diluent.

The inventive preparation of fluoromethyl-substituted heterocycles of the formula (I) is described in the examples which follow, which further illustrate the above description. However, the examples should not be interpreted in a restrictive manner.

PREPARATIVE EXAMPLES

Example 1

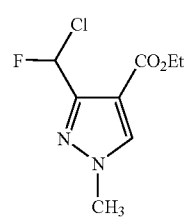

Ethyl 3-(dichloromethyl)-1-methyl-1H-pyrazole-4-carboxylate (37.9 g, 0.16 mol) and triethylamine tris(hydrofluoride) (80 g, 0.49 mol) were heated in an autoclave at 145° C. for 8 h. The reaction mixture was then diluted with 200 ml of water. The precipitated product was filtered off, washed and dried.

28.5 g (87% of theory) of ethyl 3-(difluoromethyl)-1-methyl-1H-pyrazole-4-carboxylate having a melting point of 43-46° C. were obtained.

$^1$H NMR (CDCl$_3$): δ=1.35 (t, 3H); 3.96 (t, 3H); 4.31 (q, CH$_2$); 7.10 (t, CF$_2$H); 7.90 (s, 1H) ppm. $^{19}$F NMR (CDCl$_3$): δ=−117.2 (d, J=55.4 Hz) ppm.

Example 2

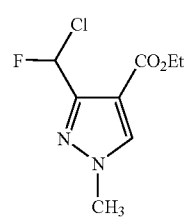

37.9 g (0.16 mol) of ethyl 3-(dichloromethyl)-1-methyl-1H-pyrazole-4-carboxylate and 80 g (0.49 mol) of triethylamine tris(hydrofluoride) were heated in an autoclave at 120° C. for 8 h. The reaction mixture was then diluted with 200 ml of water and the product extracted with ethyl acetate. The desired product was removed by chromatography from ethyl 3-(difluoromethyl)-1-methyl-1H-pyrazole-4-carboxylate and isolated.

20 g (56% of theory) of ethyl 3-(fluorochloromethyl)-1-methyl-1H-pyrazole-4-carboxylate were obtained.

$^{19}$F NMR (CDCl$_3$): δ=−133.8 (d, J=47.5 Hz) ppm.

Example 3

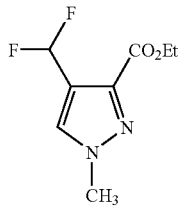

37.9 g (0.16 mol) of ethyl 4-(dichloromethyl)-1-methyl-1H-pyrazole-3-carboxylate and 80 g (0.49 mol) of triethylamine tris(hydrofluoride) were heated in an autoclave at 160° C. for 8 h. The reaction mixture was then diluted with 200 ml of water and the product extracted with ethyl acetate. The desired product was purified by chromatography and isolated.

26.8 g (75% of theory) of ethyl 4-(difluoromethyl)-1-methyl-1H-pyrazole-3-carboxylate having a melting point of 30-31° C. were obtained.

$^1$H NMR (CDCl$_3$): δ=1.37 (t, 3H); 4.07 (t, 3H); 4.31 (q, CH$_2$); 7.49 (t, CF$_2$H); 7.86 (s, 1H) ppm. $^{19}$F NMR (CDCl$_3$): δ=−117.2 (d, J=54.7 Hz) ppm.

The invention claimed is:

1. A process for preparing fluoromethyl-substituted heterocycles of formula (I)

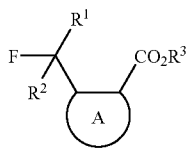

(I)

in which
R$^1$ is, fluorine or chlorine,
R$^2$ is hydrogen,
R$^3$ is C$_1$-C$_6$-alkyl,
A is a pyrazole that is substituted by R$^4$ in the 1-position, and
R$^4$ is C$_1$-C$_4$-alkyl, C$_3$-C$_6$-cycloalkyl, C$_1$-C$_4$-alkylthio-C$_1$-C$_4$-alkyl, C$_1$-C$_4$-alkoxy-C$_1$-C$_4$-alkyl, or phenyl,
comprising converting a chloromethyl-substituted heterocycle of formula (II)

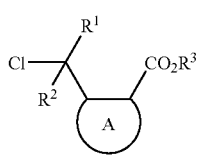

(II)

in which
R$^1$ is chlorine, and
R$^2$, R$^3$, and A are each as defined for formula (I), to a fluoromethyl-substituted heterocycle of formula (I) in the presence of a fluorinating agent selected from the group consisting of 3 HF/N(Et)$_3$ (Franz reagent), 3 HF/N(n-Bu)$_3$, and HF/pyridine (Olah's reagent) and optionally in the presence of a diluent.

2. A process according to claim 1 wherein for the chloromethyl-substituted heterocycle of formula (II),
R$^1$ is chlorine,
R$^2$ is hydrogen,
R$^3$ is C$_1$-C$_4$-alkyl,
A is a pyrazole selected from the group consisting of

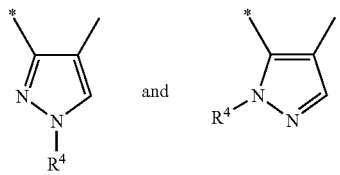

where in each case the bond marked by * is joined to the —CClR$^1$R$^2$ group and the other bond is joined to the CO$_2$R$^3$ ester group, and
R$^4$ is methyl, ethyl, n-propyl, isopropyl, cyclopropyl, cyclopentyl, cyclohexyl, or phenyl.

3. A process according to claim 1 wherein the chloromethyl-substituted heterocycle of formula (II) is selected from the group consisting of compounds of formulas (II-a), and (II-b)

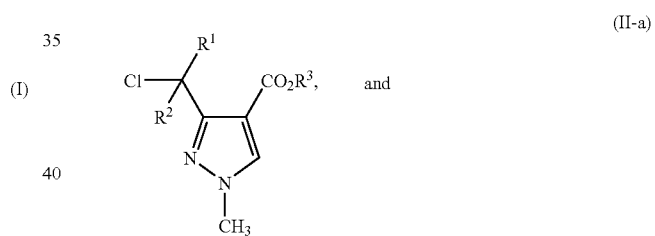

in which R$^1$, R$^2$, and R$^3$ are as defined for formula (II) in claim 1.

4. A process according to claim 3 in which R$^3$ is methyl or ethyl.

5. A process according to claim 1 wherein the fluorinating agent is 3 HF/N(Et)$_3$ (Franz reagent) or 3 HF/N(n-Bu)$_3$.

6. A process according to claim 1 that is carried out at a temperature of 80° C. to 170° C.

7. A process according to claim 1 that is carried out at a temperature of 120° C. to 150° C.

* * * * *